(12) United States Patent
De Jong (10) Patent No.: US 9,610,015 B2
(45) Date of Patent: Apr. 4, 2017

(54) RADAR APPARATUS FOR DETECTING MULTIPLE LIFE—SIGNS OF A SUBJECT, A METHOD AND A COMPUTER PROGRAM PRODUCT

(71) Applicant: Nederlandse Organisatie voor toegepast-natuurwetenschappelijk onderzoek TNO, Delft (NL)

(72) Inventor: Ard-Jan De Jong, Delft (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 209 days.

(21) Appl. No.: 14/065,965

(22) Filed: Oct. 29, 2013

(65) Prior Publication Data
US 2014/0058256 A1 Feb. 27, 2014

Related U.S. Application Data

(63) Continuation-in-part of application No. PCT/NL2012/050295, filed on Apr. 27, 2012.

(30) Foreign Application Priority Data

Apr. 29, 2011 (EP) .................................. 11164365

(51) Int. Cl.
*A61B 5/05* (2006.01)
*A61B 5/0205* (2006.01)
(Continued)

(52) U.S. Cl.
CPC ........ *A61B 5/0205* (2013.01); *A61B 5/02411* (2013.01); *A61B 5/02444* (2013.01);
(Continued)

(58) Field of Classification Search
CPC ....... A61B 5/0205; A61B 5/024; A61B 8/488; A61B 5/02411; A61B 5/02444;
(Continued)

(56) References Cited

U.S. PATENT DOCUMENTS 3,561,430 A 2/1971 Filler, Jr. et al.
4,085,740 A 4/1978 Allen, Jr.
(Continued)

FOREIGN PATENT DOCUMENTS

FR 2803508 A1 7/2001
GB 2349759 A 11/2000
(Continued)

OTHER PUBLICATIONS

Laura Antinori, "FMCW radar for life-sign detection", Radar Conference, 2009 IEEE, May 4, 2009, pp. 1-6.
(Continued)

*Primary Examiner* — Katherine Fernandez
*Assistant Examiner* — Ellsworth Weatherby
(74) *Attorney, Agent, or Firm* — Banner & Witcoff, Ltd.

(57) ABSTRACT

The invention relates to a radar apparatus for detecting a life-sign of a subject, comprising a transmitter system for emitting a transmission electromagnetic beam to the chest and/or the abdomen of a subject, a receiving system for receiving first reflected electromagnetic beam data from the chest and/or the abdomen, and a processor unit for processing the first received beam data retrieving breath activity information. The transmitter system, the receiving system and the processor are further arranged for performing a radar measurement of a superficial artery structure, such as a wrist artery, an ankle artery, a carotid artery and/or the fontanel artery for retrieving heart activity information. Thereto, the a second transmission electromagnetic beam is directed towards the superficial artery structure, the first and the
(Continued)

second transmission electromagnetic beam being transmitted from a single radar unit.

14 Claims, 6 Drawing Sheets

(51) Int. Cl.
*A61B 5/024* (2006.01)
*A61B 5/11* (2006.01)
*A61B 5/113* (2006.01)
*A61B 5/00* (2006.01)
*G01S 13/34* (2006.01)
*G01S 13/88* (2006.01)

(52) U.S. Cl.
CPC .......... *A61B 5/0507* (2013.01); *A61B 5/1102* (2013.01); *A61B 5/113* (2013.01); *A61B 5/1126* (2013.01); *A61B 5/4362* (2013.01); *G01S 13/343* (2013.01); *G01S 13/88* (2013.01); *A61B 5/6889* (2013.01)

(58) Field of Classification Search
CPC ... A61B 5/0507; A61B 5/1102; A61B 5/1126; A61B 5/113; A61B 5/4362; A61B 5/6889; G01S 13/0209; G01S 13/888; G01S 13/18; G01S 13/50; G01S 13/88; G01S 7/415; G01S 13/343
See application file for complete search history.

(56) References Cited

U.S. PATENT DOCUMENTS

| | | | |
|---|---|---|---|
| 4,219,814 A * | 8/1980 | Johnson ................ | C21B 7/24 266/86 |
| 4,513,748 A | 4/1985 | Nowogrodzki et al. | |
| 4,958,638 A * | 9/1990 | Sharpe et al. ................ | 600/407 |
| 5,361,070 A | 11/1994 | McEwan | |
| 5,573,012 A * | 11/1996 | McEwan ................ | A61B 5/024 600/428 |
| 5,749,831 A | 5/1998 | Baker | |
| 5,766,208 A | 6/1998 | McEwan | |
| 6,245,025 B1 | 6/2001 | Torok et al. | |
| 6,511,429 B1 | 1/2003 | Fatemi et al. | |
| 2003/0201894 A1 | 10/2003 | Li | |
| 2004/0267147 A1 | 12/2004 | Sullivan | |
| 2005/0128124 A1 * | 6/2005 | Greneker et al. ................ | 342/22 |
| 2006/0170584 A1 | 8/2006 | Romero et al. | |
| 2007/0171119 A1 | 7/2007 | Dwelly et al. | |
| 2008/0074307 A1 | 3/2008 | Boric-Lubecke et al. | |
| 2008/0275337 A1 | 11/2008 | Fossan et al. | |
| 2009/0048500 A1 | 2/2009 | Corn | |
| 2010/0152600 A1 * | 6/2010 | Droitcour ................ | A61B 5/05 600/534 |
| 2010/0241009 A1 * | 9/2010 | Petkie ................ | A61B 5/024 600/484 |

FOREIGN PATENT DOCUMENTS

| | | |
|---|---|---|
| WO | 9705821 A1 | 2/1997 |
| WO | 0122885 A1 | 4/2001 |
| WO | 2004057367 A1 | 7/2004 |
| WO | 2005092190 A1 | 10/2005 |
| WO | 2005099562 A1 | 10/2005 |
| WO | 2007010460 A2 | 1/2007 |
| WO | 2007063516 A2 | 6/2007 |
| WO | 2008026157 A2 | 3/2008 |
| WO | 2008057883 A2 | 5/2008 |
| WO | 2009/083017 A1 | 7/2009 |
| WO | 2012/115518 A1 | 8/2012 |

OTHER PUBLICATIONS

Immoreev I et al., "Remote monitoring of human cardiorespiratory system parameters by radar and its applications", Ultrawideband and Ultrashort Impulse Signals, 2008. UWBUSIS 2008. 4th International Conference on IEEE, dated Sep. 15, 2008, pp. 34-38.
International Search Report—PCT/NL2012/050295—Mailing Date: Aug. 9, 2012.
I. Y. Moskalenko, "Application of Centrimetre Radio Waves for Noncontact Recording of Changes in Volume of Biological Specimens", Biophysics, vol. 5, No. 2, pp. 225-228, 1960.
C. C. Johnson, and A. W. Guy, "Nonionizing Electromagnetic Wave Effects in Biological Materials and Systems", Proceedings of the IEEE, vol. 60, No. 6, pp. 692-718, Jun. 1972.
C. I. Franks, B. H. Brown, and D. M. Johnston, "Contactless Respiration Monitoring of Infants", Medical and Biological Engineering, vol. 14, No. 3, pp. 306-312, May 1976.
C. I. Franks, J. B. G. Watson, B. H. Brown, and E. F. Foster, "Respiratory Patterns and Risk of Sudden unexpected death in Infancy", Archives of Disease in Childhood, vol. 55, pp. 595-599, 1980.
A. Periasamy, and M. Singh, "Reconstruction of Cardiac Displacement Patterns on the Chest Wall by Laser Speckle Interferometry", IEEE Transactions on Medical Imaging, vol. 4, No. 1, pp. 52-57, Mar. 1985.
G. Ramachandran, and M. Singh, "Three-Dimensional reconstruction of Cardiac Displacement Patterns on the Chest Wall during the P, QRS and T-segmants of the ECG by Laser Speckle Interferometry", Medical and Biological Engineering and Computing, vol. 27, pp. 525-530, 1989.
T. Kondo, T. Uhlig, P. Pemberton, and P. D. Sly, "Laser Monitoring of Chest Wall Displacement", European Respiration Journal, vol. 10, No. 8, pp. 1865-1869, 1997.
A.J. de Jong, L. Anitori, F.A. Nennie, "Life-Sign Detection with FMCW Radar", SET-125 Symposium on Sensors and Technology for Defense against Terrorism, Mannheim, Apr. 23, 2008.
C.G. Caro, The Lancet, p. 959 (1971).
J.C. Lin, Proc. IEEE 73(2), p. 374 (1985).

* cited by examiner

RADAR APPARATUS FOR DETECTING MULTIPLE LIFE—SIGNS OF A SUBJECT, A METHOD AND A COMPUTER PROGRAM PRODUCT

CROSS-REFERENCE TO RELATED APPLICATIONS

This application is a continuation-in-part of International Application PCT/NL2012/050295 (published as WO 2012/148280 A1), filed Apr. 27, 2012, which claims priority to European Application EP 11164365.6, filed Apr. 29, 2011. Benefit of the filing date of each of these prior applications is hereby claimed. Each of these prior applications is hereby incorporated by reference in its entirety.

FIELD OF THE INVENTION

The invention relates to a radar apparatus for detecting a life-sign of a subject, comprising a transmitter system for emitting a transmission electromagnetic beam to the chest and/or the abdomen of a subject, a receiving system for receiving first reflected electromagnetic beam data from the chest and/or the abdomen, and a processor unit for processing the first received beam data retrieving breath activity information.

BACKGROUND OF THE INVENTION

Patent publication WO 2009/083017 discloses such a radar apparatus. It is known that radar measurements can be used for detecting a life-sign of a subject, such as respiration and heart beat. Radar measurements are a robust alternative to other contactless life-sign monitoring systems, e.g. based a magnetic field sensors or capacitance sensors. By performing a contactless life-sign measurement, people can automatically be monitored, e.g. infants, older people or patients.

In operation, the transmission electromagnetic beam is directed to the chest and/or the abdomen of the person to be monitored, in order to receive a reflected beam including information of breath and heartbeat.

It appears, however, that it is very difficult to reliably extract heart beat in the presence of breathing from the reflected radar signal.

SUMMARY OF THE INVENTION

It is an object of the invention to obtain a radar apparatus according to the preamble wherein heart activity information can be retrieved in a more reliable manner. Thereto, according to the invention, a radar apparatus according to claim 1 is provided.

By performing an additional radar measurement to a superficial artery structure, e.g. the person's fontanel, heart activity information can be retrieved independently from the chest and/or abdomen radar measurement, so that in the process of retrieving heart activity information, a dominant breath signal contribution is avoided.

The invention is at least partially based on the insight that the amplitude movement of the chest/abdomen due to heart activities is merely in the order of 0.1 mm, while the amplitude movement of the chest/abdomen due to lung activities is in the order of 1 cm. By making independent radar measurements, the dominant contribution of the breath can be avoided in the retrieval of heart activity information. The fontanel does not move with breath, so that a clean heartbeat response can be recorded.

Further, by performing an additional radar measurement to a superficial artery structure, a relatively high amplitude movement can be detected. As an example, the main fontanel of an infant shows an opening of usually a few square centimeters, wherein the fontanel skin moves up and down with the infant's heart rate with an amplitude in the order of 1 mm, thereby making the measurement considerably more effective.

Advantageously, the location of a superficial artery structure can be more or less independent of the position of the person to be monitored. As an example, the main fontanel will be present at more or less the same location when directing the additional beam towards the top of the person's head, no matter if the person lies on its back, stomach or side.

The invention also relates to a method of detecting a life-sign of a subject.

Further, the invention relates to a computer program product. A computer program product may comprise a set of computer executable instructions stored on a data carrier, such as a flash memory, a CD or a DVD. The set of computer executable instructions, which allow a programmable computer to carry out the method as defined above, may also be available for downloading from a remote server, for example via the Internet.

Other advantageous embodiments according to the invention are described in the following claims.

BRIEF DESCRIPTION OF THE DRAWINGS

By way of example only, embodiments of the present invention will now be described with reference to the accompanying figures in which.

It is noted that the figures show merely preferred embodiments according to the invention. In the figures, the same reference numbers refer to equal or corresponding parts.

DETAILED DESCRIPTION OF THE INVENTION

Figure 1:
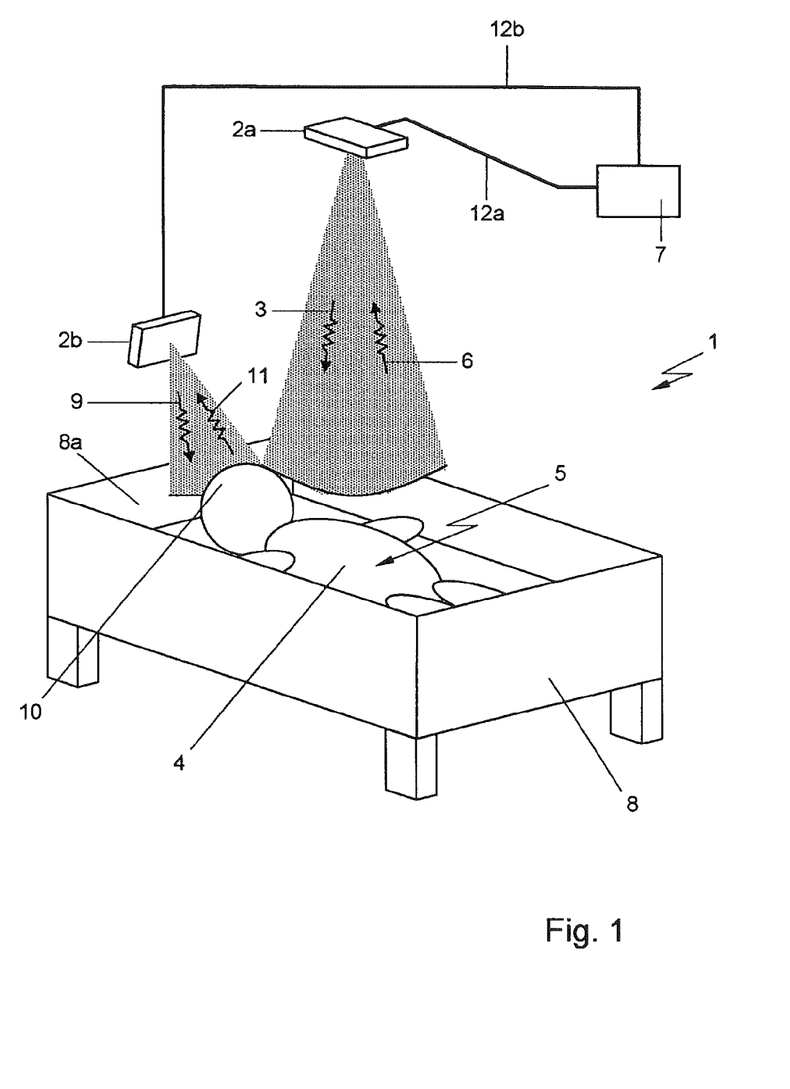
FIG. 1 shows a schematic perspective view of a radar apparatus according to a first embodiment of the invention.

FIG. 1 shows a schematic perspective view of a radar apparatus 1 according to a first embodiment of the invention. The apparatus 1 is applied for detecting a life-sign of a subject, e.g. a breathing activity and/or a heart activity. The apparatus includes a first radar unit 2a including a first transmitter system part for emitting a transmission electromagnetic beam 3 to the chest and/or the abdomen 4 of a subject 5. Further, the first radar unit 2a includes a first receiving system part for receiving data of a first reflected electromagnetic beam 6 from the chest and/or the abdomen 4. The first transmitter system part and the first receiving system part are integrated in the first radar unit 2a. The apparatus also includes a processor unit 7 for processing the first received beam data for retrieving breath activity information. The first radar unit 2a is arranged above a bed 8 wherein the subject 5 is lying.

The apparatus also includes a second radar unit 2b located above and relatively close to the front side 8a of the bed 8. The second radar unit 2b includes a second transmitter system part that is arranged for emitting an additional transmission electromagnetic beam 9 to the fontanel artery 10 of the subject 5. The second radar unit 2b also contains a second receiving system part for receiving data of a second reflected electromagnetic beam 11 from the fontanel 10. Both radar units 2a, 2b are connected, via data lines 12a, b to the processor unit 7 being further arranged for processing the second received beam data for retrieving heart activity information.

The first transmitter system part and the second transmitter system part form a transmitter system transmitting the first electromagnetic beam and the second, additional electromagnetic beam. Similarly, the first receiver system part and the second receiver system part form a receiver system receiving reflected beams from the transmitted beam and the additional transmitted beam, respectively.

Figure 2:
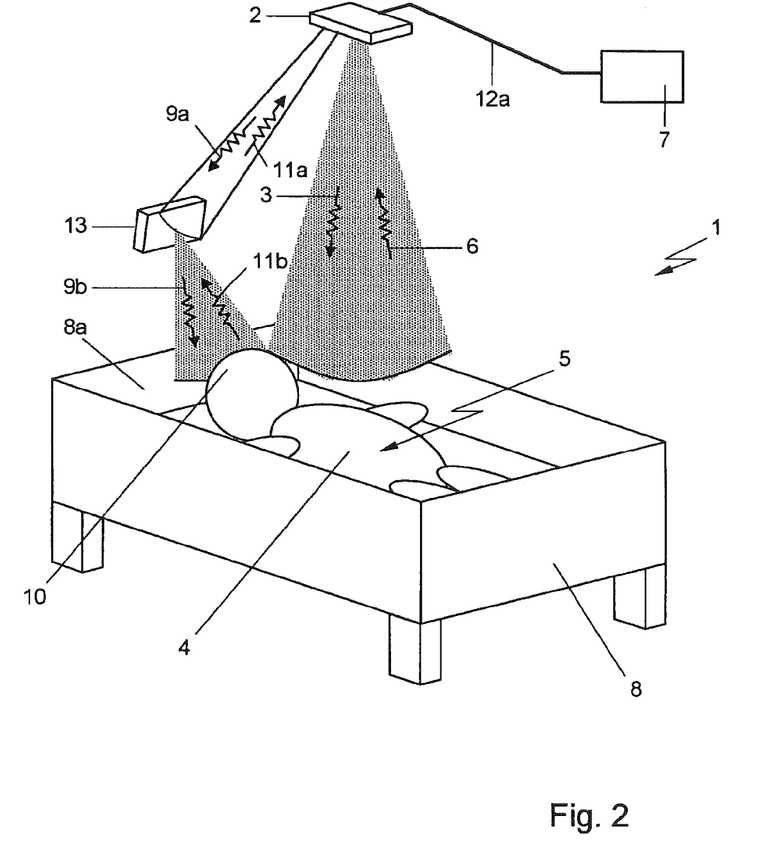
FIG. 2 shows a schematic perspective view of a radar apparatus according to a second embodiment of the invention.

FIG. 2 shows a schematic perspective view of a radar apparatus 1 according to a second embodiment of the invention. Here, the apparatus includes a single radar unit 2 containing the transmitter system and the receiver system, the unit 2 being located above the bed 8 wherein the subject 5 is lying, e.g. a distance ranging from circa 2 m to circa 2.5 m above the bed. The transmitting system transmits two beams, viz. an electromagnetic beam 3 directed to the chest and/or abdomen 4 of the subject 5 and an additional electromagnetic beam 9 directed to the fontanel 10 of the subject 5. The apparatus 1 includes a redirector 13 located above and close to the front end 8a of the bed 8. The additional beam 9a is originally directed, after emission by the transmitter unit 2 towards the redirector 13 and then redirected as a redirected beam 9b towards the fontanel 10. Similarly, the beam 11b reflected by the fontanel 10 is propagating in the reverse direction, via the redirector 13 as a redirected beam 11a towards the receiver system integrated in the single radar unit 2.

The transmitting system may include a support supporting a multiple number of transmitting antennas, such as patches. As an example, the transmitting system includes four patch antennas. Similarly, the receiving system may include a multiple number of receiving antennas, e.g. also four patch antennas. In principle, the transmitting system and the receiving system may share components, e.g. the transmitting/receiving antennas. By using a multiple number of antennas, a beam can be formed relatively efficiently, e.g. a beam having a beam width of about 25°×45°. In another embodiment according to the invention, the transmitting system is included in a first radar unit while the receiving system is included in a second radar unit.

Preferably, the redirector 13 includes a reflector reflecting the additional beam 9 towards the fontanel and backwards towards the receiving system. Alternatively, however, the redirector may in principle be implemented otherwise, e.g. by including a refractor refracting the additional beam towards the fontanel 10 of the subject 5.

It is noted that the additional beam 9a impinging the redirector 13 can be formed as a side lobe or part of the main lobe of an antenna pattern of the transmitter unit 2. Separation of the signals travelling either via the redirector 13 or directly towards the receiver system can be obtained by exploiting the difference in travelling wave length, e.g. using a so-called range gating technique, as described in more detail below, such that range bins are small enough that the signals travelling via the redirected path fall in another range bin than the signals travelling via the direct path. However, the additional beam 9a can also be formed as a separate beam generated by a multiple number of transmitter unit patches and controlled by digital beam controlling means. The reflection of the additional beam can now be separated from the first reflected electromagnetic beam 6 by digital signal processing.

Figure 3:
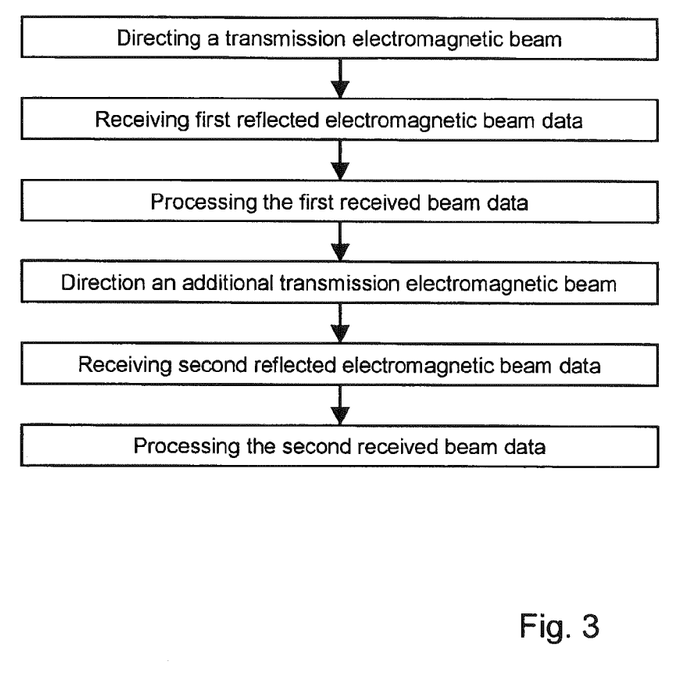
FIG. 3 shows a flow chart of a method according to an embodiment of the invention.

FIG. 3 shows a flow chart of a method according to an embodiment of the invention. The method is used for of detecting a life-sign of a subject. The method comprises a step of directing 100 a transmission electromagnetic beam to the chest and/or the abdomen of a subject having a skin surface that moves in dependence of breath activities, a step of receiving 110 first reflected electromagnetic beam data from the chest and/or the abdomen, and a step of processing 120 the first received beam data retrieving breath activity information. Further, the method comprises a step of directing 130 an additional transmission electromagnetic beam to a superficial artery structure of the subject, a step of receiving 140 second reflected electromagnetic beam data from the superficial artery structure, and a step of processing 150 the second received beam data retrieving heart activity information.

The process of detection a life-sign of a subject 5 is based on the principle of using radar measurements for observing motion of the subject 5. As an example, the transmitted radar beams 3, 9 are continuous wave (CW) radar signals. More preferably, the transmitted radar beams 3, 9 are of the frequency modulated continuous wave (FMCW) type. By applying a FMCW type radar, life-sign can be detected in separate range bins. For a given bandwidth B of a linear Frequency Modulation (FM), the range bins have size $\delta R = c/2B$ where $c=3\times10^8$ m/s is the speed of light. As an example, bandwidth B=800 MHz, so that the size of the range bins $\delta R=18.75$ cm. Thus, life-sign reflections from other range bins can be distinguished by the radar apparatus, leading to a more sensitive system. Further, FMCW technology enables measurement of both amplitude and phase for a given range gate thus combining the abilities of CW and ultra wide band (UWB) radar, offering a low-cost solution for radar life-sign detection.

The carrier frequency of the FMCW transmission beams can be selected in a frequency band ranging from circa 9.2 GHz to circa 10 GHz, e.g. 9.6 GHz. However, in principle, the carrier frequency can also be selected in another frequency band, either above 10 GHz, e.g. up to 24 GHz or higher, or below circa 9.2 GHz, e.g. down to circa 2.4 GHz or lower. A linear frequency sweep can for example be selected from a bandwidth ranging from circa 83.5 MHz to 1000 MHz, e.g. 600 MHz. As an example, a linear frequency sweep of 250 MHz or 400 MHz can be applied. The polarization of the electromagnetic emitted field can be linear and perpendicular to the long axis of the bed. However, also another electromagnetic polarization can be applied.

The chest and/or abdomen of a subject move due to heart activities and breath activities. Experiences have shown that it is hard to extract heartbeat information in the presence of breathing in a reliable manner. This is in the first place because the chest amplitude invoked by heartbeat is so much smaller, in the order of 0.1 mm, than the chest amplitude from breathing, which is in the order of 1 cm. Still, separation of heartbeat from breathing would be easy if breathing (and preferably heartbeat too) were perfectly sinusoidal. In that case, an FFT of the reflected beam data would reveal the frequencies of breathing and heartbeat.

Figure 4A:
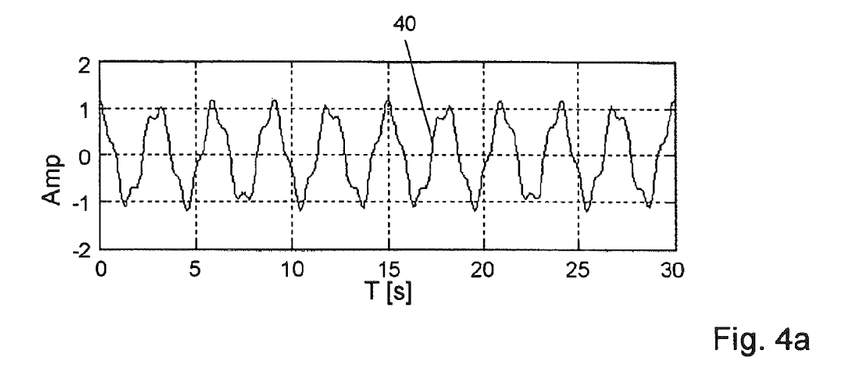
FIG. 4a shows a first prior art reflected signal.
Figure 4B:
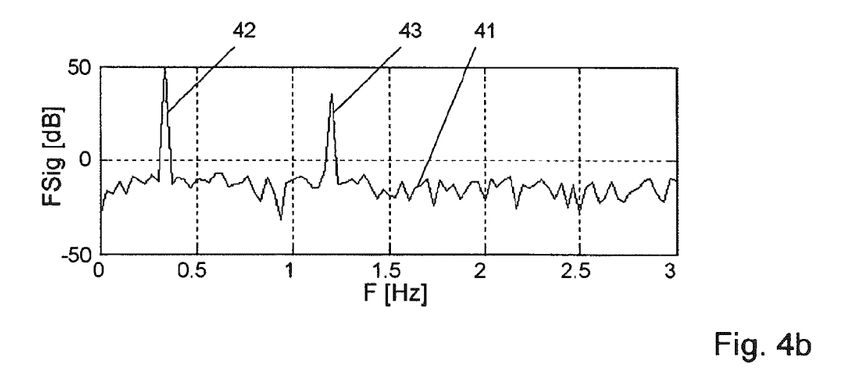
FIG. 4b shows a spectrum of the first prior art reflected signal.

FIG. 4a shows a first reflected signal 40 as a function of time T[s] including reflections of the chest and/or abdomen due to heartbeat and breath providing perfect sinusoidal amplitude behavior. Further, FIG. 4b shows a spectrum 41 of the first reflected signal 40 as a function of frequency F[Hz]. Heartbeat can be separated from breathing by distinguishing the two peaks 42, 43 in the spectrum 41 of the reflected signal, provided that the frequencies of breathing and heartbeat differ sufficiently.

Figure 4C:
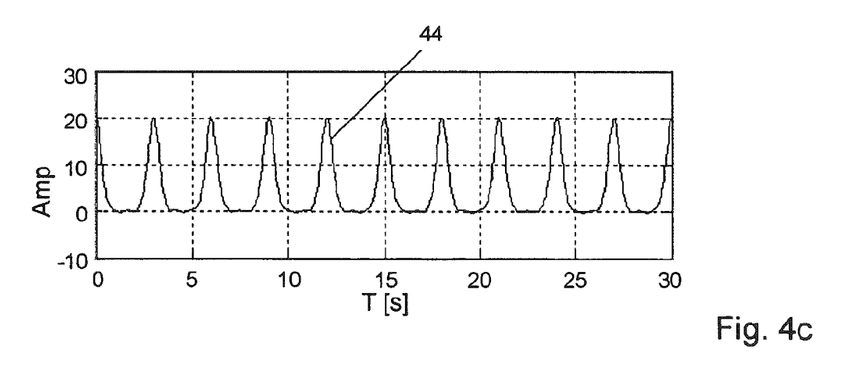
FIG. 4c shows a second prior art reflected signal.
Figure 4D:
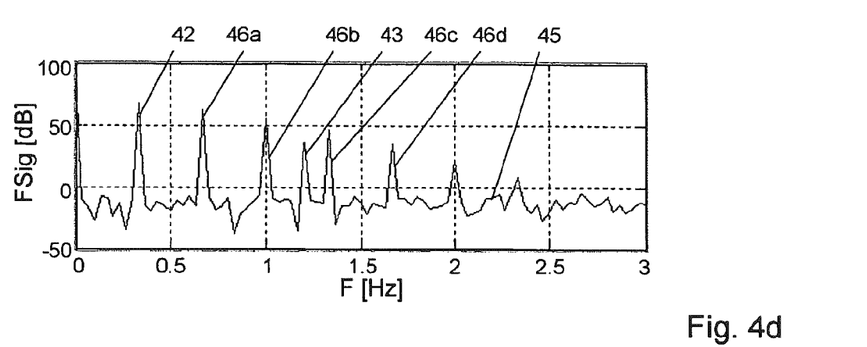
FIG. 4d shows a spectrum of the second prior art reflected signal.

However, in practice the breathing signal will not be perfectly sinusoidal. FIG. 4c shows a second reflected signal 40 as a function of time T[s] including reflections of the chest and/or abdomen due to heartbeat and breath wherein the breathing signal is perfectly periodic. FIG. 4d shows a spectrum 45 of the second reflected signal 44 as a function of frequency F[Hz]. The spectrum now contains also higher harmonics 46a-d that are very sharp peaks. Even in this situation, the heartbeat peak 43 can still be detected, provided that it does not overlap with a harmonic 46a-d from the breathing signal.

Figure 4E:
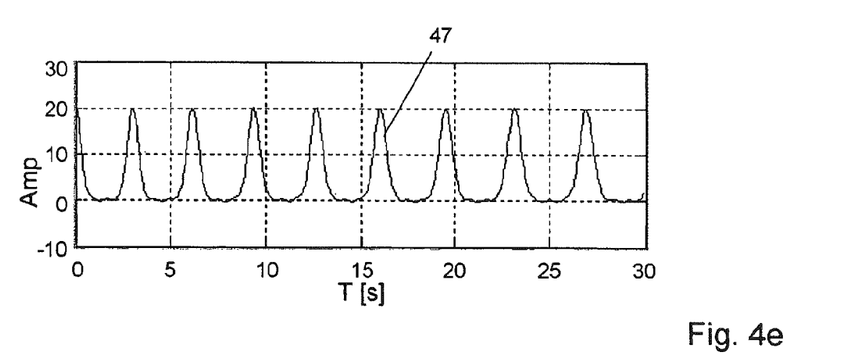
FIG. 4e shows a third prior art reflected signal.
Figure 4F:
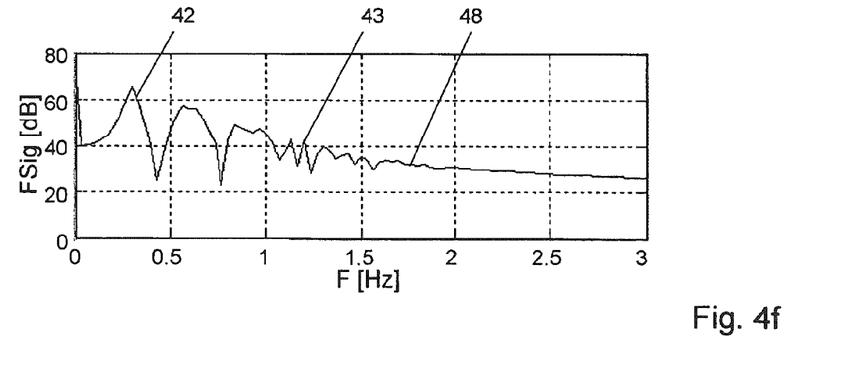
FIG. 4f shows a spectrum of the third prior art reflected signal.

FIG. 4e shows a third reflected signal 47 as a function of time T[s] including reflections of the chest and/or abdomen due to heartbeat and breath wherein the breathing signal is a-periodic, i.e. not having a constant time period. Further, FIG. 4f shows a spectrum 48 of the third reflected signal 47 as a function of frequency F[Hz]. Here, the harmonics are smeared and it becomes very difficult to extract the much weaker peak of the heartbeat frequency 43.

According to an aspect of the invention, the separate radar beam is applied for retrieving separate life-sign information. A beam is directed towards the chest and/or abdomen of a subject to retrieve breath activity information, while an additional beam is directed towards the fontanel to retrieve heart activity information.

In this context it is noted that the additional beam can also be directed to another superficial artery structure of the subject, such as a wrist artery, an ankle artery, a groin artery and/or a carotid artery.

According to a further aspect of the invention, the transmission beams have mutually different directions when approaching the subject, so as to hit the subject at the desired locations, respectively.

During at least the first 6 months of the infant's life, the main fontanel shows an opening of usually a few square centimeters. The fontanel moves up and down with the infant's heart rate. The amplitude of this movement is in the order of 1 mm, considerably more than the movement of the chest due to heartbeat. Moreover, the fontanel does not move with breath, so that a clean heartbeat response can be recorded. Also, the main fontanel will be visible when directing the additional beam towards the top of the head, no matter if the infant lies on its back, stomach or side.

When FMCW radar is used, the fontanel response can be recorded in a separate range bin, suppressing possible reflections from the rest of the body. Here, the first reflected beam data can be separated from the second reflected beam data, based on different propagation times of the respective beams.

Figure 5:
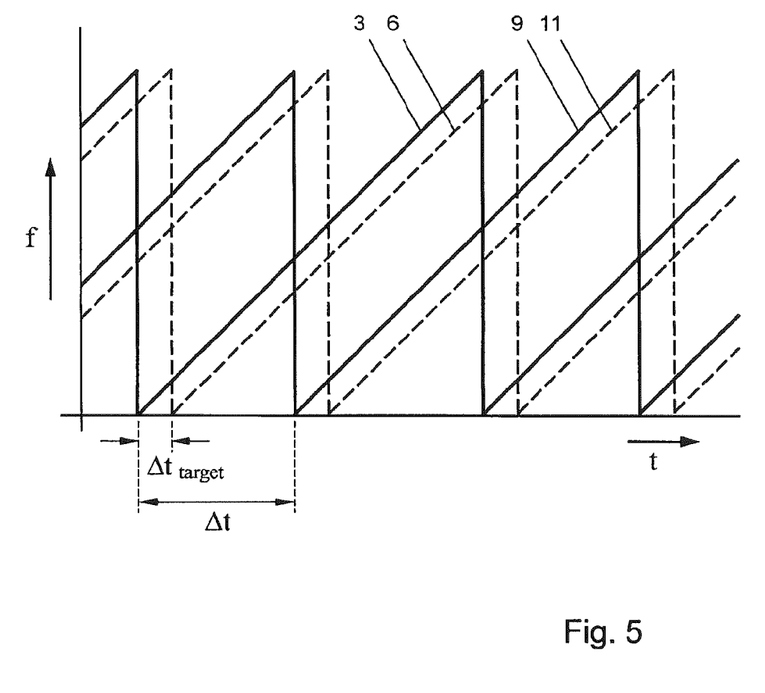
FIG. 5 shows a spectrum of transmitted and received beams.

FIG. 5 shows an instantaneous spectrum f of transmitted and received beams as a function of time t. A transmission electromagnetic beam 3 is directed to the chest and/or the abdomen 4 of a subject 5 and induces a first reflected beam 6. An additional transmission electromagnetic beam 9 is directed to the fontanel artery 10 of the subject 5 inducing a second reflected beam 11. In the shown embodiment, a FMCW radar type signal is applied. The beam 3 and the additional beam 9 have the same frequency characteristic but have a mutual delay $\Delta t$ between the sweep periods. Further, a target delay between transmission and receipt of the reflected beam depends on the propagation distance as $\Delta t_{target} = 2R/c$ wherein $2R$ is the total distance that has been traveled between transmission and receipt of the reflected beam. As an example, if the chest and/or the abdomen is located 2 meter from the single radar unit 2, the target delay is 13.3 ns. Interference of reflected beam data can be properly suppressed by using an anti-aliasing filter, suppressing the response of beat frequencies $f_b$ higher than the frequencies corresponding to a desired operational range $R_{max}$ defined by the time delay $\Delta t$ between sweep periods of the transmission beam 3 and the additional transmission beam 9. It then suffices (i) to synchronize the sweep periods of the radars so that the transmission beam and the additional transmission beam are emitted simultaneously and (ii) to keep sufficient mutual delay between the sweep periods of the radar beams. For instance, when the subject's range is 2 m, the beat frequency can be selected to be $f_b = 100$ kHz and the anti-aliasing filter suppresses signals from ranges $R > R_{max} = 6$ m or for $f_b > 300$ kHz. Now if the additional radar beam is delayed by $\Delta t > 2R_{max}/c = 40$ ns, then the radar beams will not interfere. In this example, a time period of 40 ns is very short compared to a sweep duration that is e.g. selected as $T_{up} = 80$ μs of the radar, so that this condition could be easily met, even by a considerable safety margin. For instance, $\Delta t = 1$ μs would still be small compared to the sweep duration $T_{up}$, but the suppression of mutual interference by the anti-aliasing filter would be considerably better at the corresponding range $c\Delta t = 300$ m, as this is well above the cutoff frequency of the anti aliasing window corresponding to $R_{max} = 6$ m.

In a first embodiment, the additional transmission beam 9, also called second transmission beam, is synchronized with the transmission beam 3, also called first transmission beam, with a fixed delay to avoid interference, as shown in FIG. 5. Alternatively, the first transmission beam can be synchronized with the second transmission beam, taking into account a fixed delay. It is noted that further radar beam emitting schemes can be applied, e.g. by varying the delay between the first and the second transmission beam, however such that the delay is larger than a critical interference time delay depending on a range window $R_{max}$ as described above, to avoid that reflected beam data mutually interfere.

Alternatively, an FMCW radar system can be provided that comprises
- a plurality of transmitters configured to transmit frequency swept radar signals;
- a sweep synchronization module configured to cause the transmitters to transmit the frequency swept radar signals with predetermined timing offsets between the frequency sweeps of respective ones of the transmitters;
- a receiver configured to receive a combination of reflections of the transmitted frequency swept radar signals, the receiver having an output for a received signal;
- a signal processing circuit coupled to the output and configured to separate a plurality of beat signals from respective frequency bands in the received signal respectively.

The transmission of frequency sweeps that start at different timing offsets results in reflected signals at the receiver in different frequency bands. These are separated at the receiver, for example with a filter bank. The filter bank may comprise a plurality of filters for the respective bands that each filter the same received signal. In this way, reflections of signals from different transmitters that are received at the same time can be separated, as disclosed in more detail in the European patent application 11156088.

The method for detecting a life-sign of a subject can be executed using dedicated hardware structures, such as FPGA and/or ASIC components. Otherwise, the method can also at least partially be performed using a computer program product comprising instructions for causing a processor of a computer system or a control unit to perform the above described steps of the method according to the invention. All steps can in principle be performed on a single processor. However it is noted that at least one step can be performed on a separate processor, e.g. the step of processing 150 the second received beam data retrieving heart activity information.

The processor can be arranged to perform the steps of processing first reflected electromagnetic beam data retrieving breath activity information, the first beam being reflected by the chest and/or the abdomen of a subject, and processing second received electromagnetic beam data retrieving heart activity information, the beam second beam being reflected by a superficial artery structure of the subject.

Preferably, in at least one of the processing steps breath and/or heart signal characteristics are determined.

The method and apparatus according to the invention can be applied to monitor life-signs of subject's, e.g. infants, older people or patients. The apparatus can e.g. be installed in a hospital or in a domestic environment to assist older people with every day life. Further, the method and apparatus is applicable for detecting persons inside buildings or under a pile of debris after a calamity.

It will be understood that the above described embodiments of the invention are exemplary only and that other embodiments are possible without departing from the scope of the present invention. It will be understood that many variants are possible.

As an example, the radar unit 2 can be placed above the bed wherein the subject is lying, e.g. by mounting the unit to the ceiling. However, in principle, the radar unit can also be placed at another location, e.g. on a wall facing the bed of the person to be monitored.

Further, reflection beam radar data including breath information, e.g. breath frequency, breath phase information or real time information of a breath curve, can be used to compensate for a variation in reflection beam radar data including heart activity information, wherein said variation is due to breath movements of the subject's body, thereby further improving the process of retrieving heart activity information from radar data.

Such variants will be apparent to the person skilled in the art and are considered to fall within the scope of the invention as defined in the following claims.

The invention claimed is:

1. A radar apparatus for detecting a life-sign of a subject, comprising:
   a transmitter system including a single radar unit for emitting a multiple number of transmission electromagnetic beams, wherein a first transmission electromagnetic beam is directed directly to a chest and/or abdomen of a subject, and wherein a second transmission electromagnetic beam is first directed to a redirector and redirected in a different direction from that of the first transmission electromagnetic beam to a superficial artery structure that does not move with breath;
   a receiving system for receiving first reflected electromagnetic beam data from the chest and/or the abdomen and for receiving second reflected electromagnetic beam data via the redirector from the superficial artery structure;
   a processor unit configured for separating the first reflected electromagnetic beam data from the second reflected electromagnetic beam data based on different propagation times of the respective first and second transmission electromagnetic beams; the processor unit further configured for processing the received first reflected electromagnetic beam data to retrieve breath activity information and for processing the received second reflected electromagnetic beam data to retrieve heart activity information;
   wherein the apparatus further comprises the redirector for the redirecting of the second transmission beam after emission by the single radar unit.

2. An apparatus according to claim 1, wherein the redirector includes a reflector.

3. An apparatus according to claim 1, wherein the superficial artery structure includes a wrist artery, an ankle artery, a carotid artery and/or a fontanel artery.

4. An apparatus according to claim 1, wherein the transmission beams are of the frequency modulated continuous wave (FMCW) type.

5. An apparatus according to claim 1, wherein the first and second transmission electromagnetic beams have a spectrum between 9.2 GHz and 10 GHz.

6. A method of detecting a life-sign of a subject, comprising the steps of:
   directing, from a single radar unit, a first transmission electromagnetic beam directly to a chest and/or abdomen of a subject having a skin surface that moves in dependence of breath activities;
   directing, from the single radar unit, a second transmission electromagnetic beam first to a redirector and redirecting, using the redirector, the second transmission electromagnetic beam in a different direction from that of the first transmission electromagnetic beam to a superficial artery structure of the subject that does not move with breath;
   receiving first reflected electromagnetic beam data from the chest and/or abdomen;
   receiving second reflected electromagnetic beam data via the redirector from the superficial artery structure;
   separating the first reflected electromagnetic beam data and the second reflected electromagnetic beam data based on different propagation times of the respective first and second transmission electromagnetic beams;
   processing the received first reflected electromagnetic beam data to retrieve breath activity information; and
   processing the received second reflected electromagnetic beam data to retrieve heart activity information.

7. A method according to claim 6, further comprising synchronizing the transmission of the first transmission electromagnetic beam and the second transmission electromagnetic beam such that the delay between the first and second transmission electromagnetic beams is larger than a critical interference time delay.

8. A method according to claim 6, wherein processing the received first and second reflected electromagnetic beam data comprises processing a spectrum of the received first reflected electromagnetic beam data or the received second reflected electromagnetic beam data as a function of frequency or an amplitude of the received first reflected electromagnetic beam data or the received second reflected electromagnetic beam data as a function of time.

9. An apparatus for detecting a life-sign of a subject, the apparatus comprising:
   a single radar unit configured for emitting first and second transmission electromagnetic beams, wherein the first transmission electromagnetic beam is directed directly to a chest and/or abdomen of the subject and the second transmission electromagnetic beam is first directed to a redirector and redirected in a different direction from that of the first transmission electromagnetic beam to a superficial artery structure that does not move with breath;
   a receiving system for receiving first reflected electromagnetic beam data from the chest and/or abdomen of the subject and for receiving second reflected electromagnetic beam data via the redirector from the superficial artery structure of the subject that does not move with breath;
   a non-transitory computer readable medium having a computer program embodied thereon, the computer program including instructions for causing a processor to perform the steps of:
      separating the first reflected electromagnetic beam data from the second reflected electromagnetic beam data, based on different propagation times of the respective first and second transmission electromagnetic beams;
      processing the received first reflected electromagnetic beam data to retrieve breath activity information;
      processing the received second reflected electromagnetic beam data to retrieve heart activity information; and wherein the apparatus further comprises the redirector for the redirecting of the second transmission beam after emission by the single radar unit.

10. A radar apparatus for detecting a life sign of a subject, comprising:
   a transmitter system including a single radar unit for emitting a multiple number of transmission electromagnetic beams, wherein a first transmission electromagnetic beam is directed directly to a chest and/or abdomen of a subject, and wherein a second transmission electromagnetic beam is first directed to a redirector and redirected in a different direction from that of the first transmission electromagnetic beam to a superficial artery structure that does not move with breath;
   a receiving system for receiving first reflected electromagnetic beam data from the chest and/or abdomen and for receiving second reflected electromagnetic beam data via the redirector from the superficial artery structure;
   a processor unit configured for separating the first reflected electromagnetic beam data from the second reflected electromagnetic beam data based on different propagation times of the respective transmission electromagnetic beams; the processor unit further configured for processing the first received reflected electromagnetic beam data to retrieve breath activity information and for processing the second received reflected electromagnetic beam data to retrieve heart activity information;
   wherein the apparatus further comprises the redirector for the redirecting of the second transmission electromagnetic beam after emission by the single radar unit, and
   wherein the first and second transmission electromagnetic beams have mutually different directions when approaching the subject.

11. The radar apparatus of claim 1, wherein the single radar unit is configured for emitting the first transmission electromagnetic beam and the second transmission electromagnetic beam simultaneously.

12. The method of claim 6, wherein the first transmission electromagnetic beam and the second transmission electromagnetic beam are directed simultaneously from the single radar unit.

13. The apparatus of claim 9, wherein the first electromagnetic beam and second electromagnetic beam have been transmitted simultaneously from the single radar unit.

14. The radar apparatus of claim 10, wherein the single radar unit is configured for emitting the first transmission electromagnetic beam and the second transmission electromagnetic beam simultaneously.

* * * * *